(12) United States Patent
Langer et al.

(10) Patent No.: US 7,625,580 B1
(45) Date of Patent: *Dec. 1, 2009

(54) SEMI-INTERPENETRATING OR INTERPENETRATING POLYMER NETWORKS FOR DRUG DELIVERY AND TISSUE ENGINEERING

(75) Inventors: Robert S. Langer, Newton, MA (US); Jennifer Elisseeff, Baltimore, MD (US); Kristi Anseth, Boulder, CO (US); Derek Sims, Greensboro, NC (US)

(73) Assignee: Massachusetts Institute of Technology, Cambridge, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 09/724,382

(22) Filed: Nov. 28, 2000

(51) Int. Cl.
*A61K 2/02* (2006.01)
(52) U.S. Cl. .................. 424/426; 523/113; 523/114; 523/115; 523/116
(58) Field of Classification Search ................. 424/425, 424/486, 423, 426; 525/903, 937; 523/113, 523/114, 115, 116
See application file for complete search history.

(56) References Cited

U.S. PATENT DOCUMENTS

| | | | |
|---|---|---|---|
| 5,041,138 A * | 8/1991 | Vacanti et al. | |
| 5,115,020 A | 5/1992 | Muramoto et al. | |
| 5,334,640 A | 8/1994 | Desai et al. | |
| 5,514,378 A | 5/1996 | Mikos et al. | |
| 5,567,435 A | 10/1996 | Hubbell et al. | |
| 5,700,848 A * | 12/1997 | Soon-Shiong et al. | |
| 5,709,854 A | 1/1998 | Griffith-Cima et al. | |
| 5,837,752 A | 11/1998 | Shastri et al. | |
| 5,900,245 A | 5/1999 | Sawhney et al. | |

(Continued)

FOREIGN PATENT DOCUMENTS

WO    WO 93/17669    9/1993

(Continued)

OTHER PUBLICATIONS

Matsuda et al., "Photoinduced Prevention of Tissue Adhesion," *ASAIO Journal*, 38(1):M154-M157 (1992).

(Continued)

*Primary Examiner*—Carlos A. Azpuru
(74) *Attorney, Agent, or Firm*—Choate, Hall & Stewart LLP (57) ABSTRACT

Compositions for tissue engineering and drug delivery have been developed based on solutions of two or more polymers which form semi-interpenetrating or interpenetrating polymer networks upon exposure to active species following injection at a site in a patient in need thereof. The polymers crosslink to themselves but not to each other; semi-interpenetrating networks are formed when only one of the polymers crosslink. The resulting viscous solutions retain the biologically active molecules or cells at the site of injection until release or tissue formation, respectfully, occurs.

As a result of studies conducted with polymer-cell suspensions forming interpenetrating polymer networks, it has been determined that polymer solutions can be formulated wherein the active species is provided by exposure of the polymer solution to an exogenous source of active species, typically electromagnetic radiation, preferably light. Studies demonstrate that light will penetrate through skin, body fluids (such as synovial fluid) and membranes and polymerize the polymer solutions. The polymer solutions can be crosslinked ionically or covalently, to form a hydrogel, semi-interpenetrating polymer network or an interpenetrating polymer network.

12 Claims, 5 Drawing Sheets

U.S. PATENT DOCUMENTS

| | | | |
|---|---|---|---|
| 5,902,599 A * | 5/1999 | Anseth et al. | 424/426 |
| 6,077,916 A * | 6/2000 | Laurencin et al. | 525/419 |
| 6,224,893 B1 * | 5/2001 | Langer et al. | |
| 6,312,725 B1 * | 11/2001 | Wallace et al. | 424/484 |

FOREIGN PATENT DOCUMENTS

| | | |
|---|---|---|
| WO | WO 94/25080 | 11/1994 |
| WO | WO 96/40304 | 12/1996 |
| WO | WO 97/17038 | 5/1997 |

OTHER PUBLICATIONS

Sims et al., "Injectable Cartilage Using Polyethylene Oxide Polymer Substrates," *Plastic & Reconstructive Surgery*, 98(5):843-850 (1996).

Steinleitner et al., "An Evaluation of Flowgel* as an Intraperitoneal Barrier for Prevention of Postsurgical Adhesion Reformation," *Fertility and Sterility*, 57(2):305-308 (1992).

Steinleitner et al., "Poloxamer 407 as an Intraperitoneal Barrier Material for the Prevention of Postsurgical Adhesion Formation and Reformation in Rodent Models for Reproductive Surgery," *Obstetrics & Gynecology*, 77(1):48-52 (1991).

* cited by examiner

SEMI-INTERPENETRATING OR INTERPENETRATING POLYMER NETWORKS FOR DRUG DELIVERY AND TISSUE ENGINEERING

The United States government has certain rights in this invention by virtue of grant AR08387 NIH Fellowship 23464 to Robert S. Langer.

This application claims priority to U.S. patent application Ser. No. 08/862,740 filed May 23, 1997 (now U.S. Pat. No. 6,224,893) and to U.S. Provisional Application Ser. No. 60/041,881 filed Apr. 11, 1997, Express Mail Label No. EM290166797US, the entire contents of both of which are herein incorporated by reference.

BACKGROUND OF THE INVENTION

The present invention is generally in the area of using polymeric semi-interpenetrating and interpenetrating polymer network compositions and photocrosslinkable polymeric hydrogels in medical treatments, especially joint resurfacing and plastic surgery and delivery of drugs.

Congenital Defects

Many congenital defects, especially in the urogenital areas, require surgical correction. Examples include treatment of reflux and urinary incontinence. WO 94/25080 by Massachusetts Institute of Technology describes the use of injectable polysaccharide-cell compositions for delivering isolated cells by injection, which then form new tissue that is effective as a bulking agent. The polymers that are described crosslink ionically, as a function of ionic strength, temperature, pH, or combinations thereof. WO 96/40304 by Reprogenesis describes similar applications of polymeric hydrogels formed by covalent crosslinking, for example, by photopolymerization of the injected polymer-cell suspension using a catheter or during surgery.

Craniofacial Contour Deformities

Craniofacial contour deformities, whether traumatic, congenital, or aesthetic, currently require invasive surgical techniques for correction. Furthermore, deformities requiring augmentation often necessitate the use of alloplastic prostheses which suffer from problems of infection and extrusion. Correction of these defects and irregularities remain a difficult and controversial problem. Sims, et al., reported in *Plastic Reconstructive Surgery* 98:845 (1996), the formation of new cartilage from injected polyethylene oxide-cell suspensions, and suggested that this technology would be useful in plastic surgery.

Replacement or Repair of Cartilaginous Surfaces

The aging population, especially of those active in sports and in jobs creating stress on joints, have little recourse at this time for repair or replacement of cartilage. Arthroscopic surgery can be used to remove torn cartilage but highly invasive and painful surgery is required for repair or replacement of a joint having little cartilage left. In most cases a prosthetic device must be used to replace the entire joint, following destruction of the smooth cartilaginous surface which normally allows for free movement of the abutting joint surfaces. As described in U.S. Pat. No. 5,514,378 to Vacanti, et al., it has been proposed to create new joint surfaces using a synthetic polymeric mesh seeded with chondrocytes, which forms new cartilage as the polymer degrades. Although this is promising, the seeded mesh must still be implanted surgically.

There is a need for improved injectable polymer-cell compositions which are biocompatible and biodegradable for delivering isolated cells by injection. There is a further need for less invasive means of covalently crosslinking polymer-cell suspensions following injection.

Accordingly, it is an object of the present invention to provide methods and compositions for injection of cells to form cellular tissues and cartilaginous structures, based on interpenetrating networks of synthetic polymers.

It is a further object of the invention to provide improved compositions to form cellular tissues and cartilaginous structures including non-cellular material which will degrade and be removed to leave tissue or cartilage that is histologically and chemically the same as naturally produced tissue or cartilage.

It is another object of the present invention to provide compositions for and a method for covalent crosslinking a polymer-cell suspension for formation of new tissue following injection.

SUMMARY OF THE INVENTION

Compositions for tissue engineering and drug delivery have been developed based on solutions of two or more polymers which form semi-interpenetrating or interpenetrating polymer networks upon exposure to active species following injection at a site in a patient in need thereof. The polymers crosslink to themselves but not to each other; semi-interpenetrating networks are formed when only one of the polymers crosslink. The resulting viscous solutions retain the biologically active molecules or cells at the site of injection until release or tissue formation, respectfully, occurs.

As a result of studies conducted with polymer-cell suspensions forming interpenetrating polymer networks, it has been determined that polymer solutions can be formulated wherein the active species is provided by exposure of the polymer solution to an exogenous source of active species, typically electromagnetic radiation, preferably light. Studies demonstrate that light will penetrate through skin, body fluids (such as synovial fluid) and membranes and polymerize the polymer solutions. The polymer solutions can be crosslinked ionically or covalently, to form a hydrogel, semi-interpenetrating polymer network or an interpenetrating polymer network.

DETAILED DESCRIPTION OF THE INVENTION

Techniques of tissue engineering employing biocompatible polymer scaffolds hold promise as a means of creating alternatives to prosthetic materials currently used in plastic surgery and joint repair or replacement, as well as formation of organ equivalents to replaced diseased, defective, or injured tissues.

Interpenetrating networks ("IPN") are defined as networks where two components are crosslinked, but not to each other. As described herein, in one embodiment, semi-interpenetrating networks of synthetic and/or natural polymers are used as the polymeric support for cells to be injected. Semi-interpenetrating networks are defined as solutions that include two independent components, where one component is a crosslinked polymer and the other component is a non-crosslinked polymer. The crosslinked polymer preferably constitutes between about 10 and 90% by weight of the semi-interpenetrating network composition.

The semi-interpenetrating polymer networks are preferably prepared from hydrophilic polymers. In one embodiment, the polymer networks include a hydrophilic polymer with groups crosslinkable with active species and/or ionically crosslinkable groups, and a hydrophilic polymer with no active species or ionically crosslinkable groups.

In a second embodiment, cells are suspended in a polymer solution which can be crosslinked by active species generation, preferably by photoactivation. The suspension is injected at the site where new tissue is to be formed. Light is then applied externally to the skin to crosslink the injected polymer. This method is based on the discovery that combinations of polymers and photoinitiators (in a concentration not toxic to the cells, less than 0.1% by weight, more preferably between 0.05 and 0.01% by weight percent initiator) will crosslink upon exposure to light equivalent to between one and 3 mWatts/cm$^2$ applied to the skin of nude mice. Although discussed herein principally with regard to administration of a light source external to the skin, this should be interpreted as equally applicable to light applied through tissues, for example, from a catheter in a blood vessel adjacent to a tissue where the polymer-cell suspension has been injected, or in the synovial space adjacent to a cartilaginous surface to be repaired or replaced with injected polymer-cell suspension.

Polymer Compositions

The polymer compositions can consist solely of covalently crosslinkable polymers, as described in WO96/40304, in combination with an effective but non-toxic about of photoinitiator to allow crosslinking using radiation provided by an external source, or blends of covalently and ionically crosslinkable or hydrophilic polymers which when exposed to radiation form semi-interpenetrating networks having cells suspended therein.

Ionically Crosslinkable and Hydrophilic Polymers

As used herein, "hydrophilic polymers" are defined as polymers with a solubility of at least ten grams/liter of an aqueous solution at a temperature of between about 0 and 50° C. Aqueous solutions can include small amounts of water-soluble organic solvents, such as dimethylsulfoxide, dimethylformamide, alcohols, acetone, and/or glymes.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Examples of materials which can be used to form a hydrogel include modified alginates. Alginate is a carbohydrate polymer isolated from seaweed, which can be crosslinked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or ε-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a firm gel, which are derivatized with hydrophobic, water-labile chains, e.g., oligomers of ε-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., *Obstetrics & Gynecology*, 77:48-52 (1991); and Steinleitner et al., *Fertility and Sterility*, 57:305-308 (1992). Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Aliphatic hydroxy groups are not considered to be reactive groups for the chemistry disclosed herein. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

In the embodiment wherein modified alginates and other anionic polymers that can form hydrogels which are malleable are used to encapsulate cells, the hydrogel is produced by cross-linking the polymer with the appropriate cation, and the strength of the hydrogel bonding increases with either increasing concentrations of cations or of polymer. Concentrations from as low as 0.001 M have been shown to cross-link alginate. Higher concentrations are limited by the toxicity of the salt.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically crosslinkable groups. Methods for modifying hydrophilic polymers to include these groups are well known to those of skill in the art.

The polymers may be intrinsically biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 daltons or below. Usable, but less preferable for general use because of intrinsic biodegradability, are water-soluble natural polymers and synthetic equivalents or derivatives, including polypeptides, polynucleotides, and degradable polysaccharides.

The polymers can be a single block with a molecular weight of at least 600, preferably 2000 or more, and more preferably at least 3000. Alternatively, the polymers can include can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Covalently Crosslinkable Polymer Solutions

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., *ASAID Trans.*, 38:154-157 (1992).

The term "active species polymerizable group" is defined as a reactive functional group that has the capacity to form additional covalent bonds resulting in polymer interlinking upon exposure to active species. Active species include free radicals, cations, and anions. Suitable free radical polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In one embodiment, the active species polymerizable groups are preferably located at one or more ends of the hydrophilic polymer. In another embodiment, the active species polymerizable groups are located within a block copolymer with one or more hydrophilic polymers forming the individual blocks. The preferred polymerizable groups are acrylates, diacrylates, oligoacrylates, dimethacrylates, oligomethacrylates, and other biologically acceptable photopolymerizable groups. Acrylates are the most preferred active species polymerizable group.

In general, the polymers are at least partially soluble in aqueous solutions, such as water, buffered salt solutions, or aqueous alcohol solutions. Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Preferably, the hydrophilic polymers that include active species or crosslinkable groups include at least 1.02 polymerizable or crosslinkable groups on average, and, more preferably, each includes two or more polymerizable or crosslinkable groups on average. Because each polymerizable group will polymerize into a chain, crosslinked hydrogels can be produced using only slightly more than one reactive group per polymer (i.e., about 1.02 polymerizable groups on average). However, higher percentages are preferable, and excellent gels can be obtained in polymer mixtures in which most or all of the molecules have two or more reactive double bonds. Poloxamines, an example of a hydrophilic polymer, have four arms and thus may readily be modified to include four polymerizable groups.

Photoinitiators

Polymerization is preferably initiated using photoinitiators. Photoinitiators that generate a active species on exposure to UV light are well known to those of skill in the art. Active species can also be formed in a relatively mild manner from photon absorption of certain dyes and chemical compounds.

These groups can be polymerized using photoinitiators that generate active species upon exposure to UV light, or, preferably, using long-wavelength ultraviolet light (LWUV) or visible light. LWUV and visible light are preferred because they cause less damage to tissue and other biological materials than UV light. Useful photoinitiators are those which can be used to initiate polymerization of the macromers without cytotoxicity and within a short time frame, minutes at most and most preferably seconds.

Exposure of dyes and cocatalysts such as amines to visible or LWUV light can generate active species. Light absorption by the dye causes the dye to assume a triplet state, and the triplet state subsequently reacts with the amine to form a active species which initiates polymerization. Polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

Photopolymerization of these polymer solutions is based on the discovery that combinations of polymers and photoinitiators (in a concentration not toxic to the cells, less than 0.1% by weight, more preferably between 0.05 and 0.01% by weight percent initiator) will crosslink upon exposure to light equivalent to between one and 3 mWatts/cm$^2$ applied to the skin of nude mice.

Figure 1:
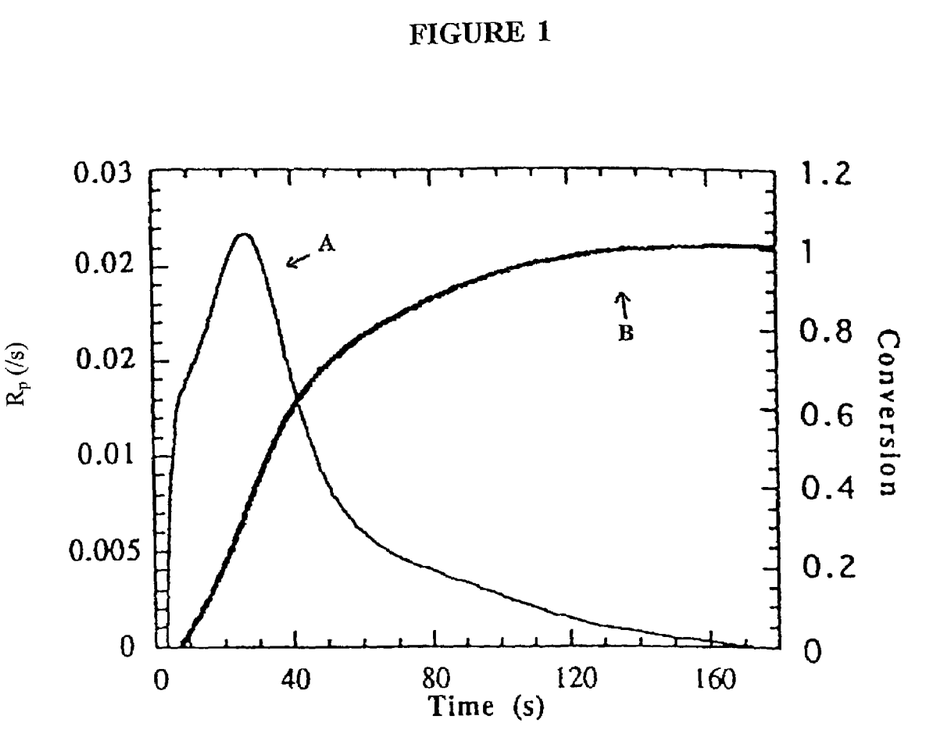
FIG. 1 graphically depicts the rate of polymerization, A, and percent conversion of a polymerizable solution to a polymer matrix, B, over time with a photoactive initiator and ultraviolet light.

FIG. 1 demonstrates the extent of conversion of a polymer solution over time as compared to the rate of polymerization.

Source of Cells

Cells can be obtained directed from a donor, from cell culture of cells from a donor, or from established cell culture lines. In the preferred embodiment, cells of the same species and preferably immunological profile are obtained by biopsy, either from the patient or a close relative, which are then grown to confluence in culture using standard conditions and used as needed. If cells that are likely to elicit an immune reaction are used, such as human muscle cells from immunologically distinct individual, then the recipient can be immunosuppressed as needed, for example, using a schedule of steroids and other immunosuppressant drugs such as cyclosporine. However, in the most preferred embodiment, the cells are autologous.

In the preferred embodiments, cells are obtained directly from a donor, washed and implanted directly in combination with the polymeric material. The cells are cultured using techniques known to those skilled in the art of tissue culture. Cells obtained by biopsy are harvested and cultured, passaging as necessary to remove contaminating cells. Isolation of chondrocytes and muscle cells is demonstrated in WO 94/25080, the disclosure of which is incorporated herein.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production.

Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labelled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

Biologically Active Materials Added to the Polymer Suspensions.

The polymer solutions can be used for drug delivery. Examples of materials to be incorporated into the polymer solutions are proteins, polysaccharides, nucleic acid molecules, and synthetic organic or inorganic molecules. These may be useful for therapeutic, prophylactic or diagnostic purposes. Drugs may include antibiotics, antivirals, chemotherapeutic agents, anti-angiogenic agents, hormones, drugs having an effect on vascular flow, anti-inflammatories, and many others routinely used.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-polymer suspension prior to formation of implant or transplantation. Alternatively, the hydrogel could be modified to bind humoral factors or signal recognition sequences prior to combination with isolated cell suspension.

Blends of Ionically and Covalently Crosslinkable Polymers

In a preferred embodiment, the polymer solution is formed of two or more polymers, which crosslink to form a semi-interpenetrating network. For example, the blend could include PEO, which is ionically crosslinkable, and diamethacrylated PEO, in a range of between 10 and 40% by weight covalently crosslinkable polymer in the preferred embodiment. Alternatively, blends of two covalently crosslinkable polymers can be used, selected on the basis that they form a network of crosslinked homopolymers, not to each other. Advantages of the semi-interpenetrating networks include that the diffusion of non-crosslinked polymer can provide advantages degradation properties, and enhance mechanical properties, especially for use in plastic surgery.

Cell Suspensions

Preferably the polymer is dissolved in an aqueous solution, preferably a 0.1 M potassium phosphate solution, at physiological pH, to a concentration forming a polymeric hydrogel. The isolated cells are suspended in the polymer solution to a concentration of between 1 and 50 million cells/ml, most preferably between 10 and 20 million cells/ml.

Methods of Implantation

In the preferred embodiment, the molecules to be delivered or cells are mixed with the polymer solution and injected directly into a site where it is desired to implant the molecules or cells, prior to crosslinking of the polymer to form the hydrogel matrix.

The site, or sites, where molecules or cells are to be injected is determined based on individual need, as is the requisite amount of molecules or number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma or burns. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscope or thoracoscope to any intraperitoneal or extraperitoneal or thoracic organ. For example, the suspension could be injected in the region of the gastro-esophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

The material can also be used to treat vesicoureteral reflux. In addition to its use for the endoscopic treatment of reflux, the system of injectable autologous muscle cell may also be applicable for the treatment of other medical conditions, such as urinary and rectal incontinence, dysphonia, plastic reconstruction, and wherever an injectable permanent biocompatible material is needed. Methods for using an injectable polymer for delivering isolated cells via injection are described for example in WO 94/25080.

In addition to the use of the cell-polymer suspension for the treatment of reflux and incontinence, the suspension can also be applied to reconstructive surgery, as well as its application anywhere in the human body where a biocompatible permanent injectable material is necessary. The suspension can be injected endoscopically, for example through a laryngoscope for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

This technology can be used for other purposes. For example, custom-molded cell implants can be used to reconstruct three dimensional tissue defects, e.g., molds of human ears could be created and a chondrocyte-hydrogel replica could be fashioned and implanted to reconstruct a missing ear. Cells can also be transplanted in the form of a three-dimensional structure which could be delivered via injection.

Application of Active Species Generators

In the preferred embodiment using photopolymerizable polymers, the light is applied externally to the tissue where the polymer suspension has been injected. Biologically active molecules or cells are suspended in a polymer solution which can be crosslinked by active species generation, preferably by photoactivation. The suspension is injected at the site where new tissue is to be formed or drug to be released. Light is then applied externally to the skin to crosslink the injected polymer. This method is based on the discovery that combinations of polymers and photoinitiators (in a concentration not toxic to the cells, less than 0.1% by weight, more preferably between 0.05 and 0.01% by weight percent initiator) will crosslink upon exposure to light equivalent to between one and 3 mWatts/cm$^2$ applied to the skin of nude mice. Although discussed herein principally with regard to administration of a light source external to the skin, this should be interpreted as equally applicable to light applied through tissues, for example, from a catheter in a blood vessel adjacent to a tissue where the polymer-cell suspension has been injected, or in the synovial space adjacent to a cartilaginous surface to be repaired or replaced with injected polymer-cell suspension.

The depth of penetration can be controlled by the wavelength of the light utilized to cause the photopolymerization. For example, visible light penetrates deeper through tissue than UV light. Penetration through tissue can range from microns to one cm, 1 cm occurring with visible light. In a preferred embodiment, radiation of 200 to 700 nm wavelength is used to create active species and polymerize the network.

A minimum of 0.01 mW/cm$^2$ intensity is needed to induce polymerization. Maximum light intensity can range from one to 1000 mW/cm$^2$ depending upon the wavelength of radiation. Higher light intensities can be exposed to tissue for example, with longer wavelength, visible light which causes less tissue/cell damage than shortwave UV light. In dental applications, blue light (470-490 nm) is used at intensities of 100 to 400 mW/cm$^2$ clinically.

The intensity of the radiation is controlled to minimize cell exposure in the case of injection of polymer-cell suspensions. In the nude mouse, the cells were exposed to 1 to 3 mW/cm$^2$ UVA light. By knowing the thickness of the tissue and the decrease in radiation intensity as it passes through tissue, one can predict and control the light intensity to which the cells are exposed. It is desirable to have the cell-polymer suspension exposed to light of the minimum intensity needed to cause the formation of active species and polymerization.

The teachings of the cited publications are indicative of the level of skill and the general knowledge of those skilled in the art. To the extent necessary, the publications are specifically incorporated herein by reference.

Where appropriate, the following definitions are to be used.

"Electromagnetic Radiation" as used herein refers to energy waves of the electromagnetic spectrum including, but not limited to, x-ray, ultraviolet, visible, infrared, far infrared, microwave and radio-frequency.

"Visible light" as used herein refers to energy waves having a wavelength of at least approximately $4.0 \times 10^{-5}$ cm.

"Ultraviolet light" as used herein refers to energy waves having a wavelength of at least approximately $1.0 \times 10^{-5}$ cm but less than $7.0 \times 10^{-5}$ cm.

"Ultraviolet light" as used herein refers to energy waves having a wavelength of at least approximately $1.0 \times 10^{-5}$ cm but less than $4.0 \times 10^{-5}$ cm.

"Blue light" as used herein refers to energy waves having a wavelength of at least approximately $4.5 \times 10^{-5}$ cm but less than $4.9 \times 10^{-5}$ cm.

"Radiation source" as used herein refers to a source of radiation (as defined above). Examples include, but are not limited to, lamps, the sun, blue lamps, and ultraviolet lamps.

The present invention will be further understood by reference to the following non-limiting examples.

Example 1

Ex Vivo Experiments

Ex vivo experiments were performed to obtain quantitative data on polymerization rates and depth of polymerization under skin, fat and muscle.

First, light intensity was measured in the skin. Skin was harvested from a rat and photopolymerization was tested under the epidermis and dermis with no subcutaneous fat, with subcutaneous fat and intramuscular under the skin and fat.

TABLE 1

Experimentally measured light intensity at different levels in the rat skin and the effect of wavelength on the light penetration.

| Injection Site (skin thickness) | UVA (% light transmitted) | Blue Light (% light transmitted) |
|---|---|---|
| Subcutaneous (~1 mm) | 4.0% | 11.6% |
| Subcutaneous Fat (~1.6 mm) | 1.6% | 4.8% |
| Subcutaneous Fat and Muscle (5.0 mm) | 0.7% | 1.9% |

After light intensity was determined, the ability to induce photopolymerization under various thickness skin layers was assessed. Poly(ethylene glycol) (MW 3400, Polysciences, Warrington, Pa.), end capped with a methacrylate group at both ends (Shearwater Polymers, Huntsville, Ala.) was polymerized with ultraviolet, blue and visible light as described in U.S. Pat. No. 5,567,435 to Hubbel et al., herein incorporated by reference. A differential scanning calorimeter equipped with a photocalorimeter accessor (Perkin Elmer, Norwalk, Conn.) was used to photopolymerize under the skin layers and obtain polymerization rates.

Figure 2:
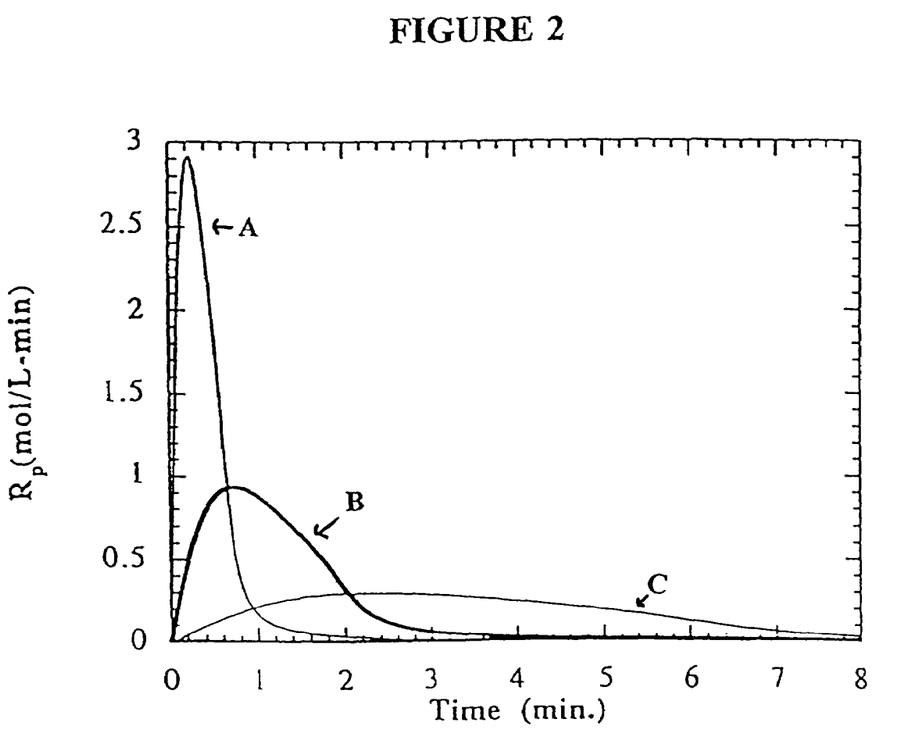
FIG. 2 graphically sets for the calculated rate (time in minutes) of photopolymerization of a polymerizable solution under the subcutaneous, A, subcutaneous and fat, B, and subcutaneous and fat and muscle, C, layers of rat skin based upon the penetration of light through these layers.

FIG. 2 predicts the rate of photopolymerization of a polymerizable solution under the subcutaneous, A, subcutaneous and fat, B, and subcutaneous and fat and muscle, C, layers of rat skin. Hence, the polymerization time can be varied from seconds to minutes depending on the wavelength of light, depth of injection, intensity of the incident light, and initiator type and concentration. Even with minimal transmittance of light (e.g., 100 mW/cm$^2$ at the skin surface, but approximately 0.6 mW/cm$^2$ at the intramuscular layer), polymerization occurs. In essence, polymerization is feasible if the intensity of light reaching the injected polymer solution is at least 0.01 mW/cm$^2$. The main influence of light attenuation is the increase in polymerization time and decrease in polymerization rate.

Example 2

In Vivo Experiments

Nude mice were injected subcutaneously with a polymerizable solution containing DMA as described in Example 1 and exposed to UVA light from a tanning bed at an intensity of 3-5 mW/cm$^2$ for four minutes. The resulting hydrogel was palpated and determined to have polymerized from a liquid to a solid. Controls not exposed to light did not polymerize. In order to further confirm polymerization, the mice were sacrificed and the hydrogel and surrounding skin and tissue were excised. Polymerization was confirmed by swelling the hydrogel in water.

Example 3

Drug Delivery Vehicle

The cogelation of the methacrylated mixed anhydride of succinic acid and poly(ethylene oxide) and dimethacrylate (PEOD) is useful for extending the release of hydrogels. This increases the crosslinking density of PEO networks. A labile anhydride bond in addition to the ester bonds attaching the methacrylate groups of PEO is present in the resulting hydrogels increasing the mechanisms and rate by which hydrolytic degradation may occur.

This example describes the creation of a photopolymerized succinic acid anhydride/PEO polymer and release of compounds from this polymer. The example is divided as follows: A) mixing succinic acid with polymerizable methacrylate groups, B) mixing release compound with a polymerizable solution of succinic dimethacrylate and PEOD, C) testing swelling, and D) measuring release over time. PEOD was also cogelled with 1,2-(dihydroxyethylene)bisacrylamide and Diallyl-tartardiamide.

A. Making Succinic Dimethacrylate (SAD)

Succinic acid was dissolved in anhydrous dimethyl sulfoxide (DMSO, Aldrich, Steizenhofen, Germany) and an excess of methacrylic anhydride (Aldrich, Steizenhofen, Germany) was added. The reaction mixture was purged with argon and heated to 40° C. for 24 h. The reaction mixture was cooled to room temperature and precipitated by adding to a 10× excess of ether. The precipitate was vacuum filtered and dried under vacuum.

Infrared spectroscopy was used to monitor substitution of the succinic acid carboxylic acid groups. Comparison of the infrared spectra of succinic acid before and after reaction with methacrylic anhydride shows the disappearance of the wide acid peak centered at 3100 cm$^{-1}$ (i.e., showing the disappearance of the succinic acid carboxylic acid groups).

B. Mixing Release Compound in a Polymerizable Solution

PEOD of MW's 1000 (Polysciences, Warrington, Pa.) and 3400 (Shearwater Polymers, Huntsville, Ala.) were utilized as a polymerizeable solution. Varying percentages of PEOD and succinic dimethacrylate (SAD) were dissolved in water to form a 50/50% w/v polymerizable solution using approximately 100 mg polymerizable solution. Polymerizable solutions containing more than 40% succinic dimethacrylate were heated on a hot plate for 2-4 seconds before photopolymerization in order to dissolve the SAD.

Bovine serum-albumin (BSA, Sigma, Steizenhofen, Germany) was added to the 50/50% w/v polymerizable solution solutions and vortexed. The polymer solution was subsequently exposed to UV radiation (EFOS Ultracure) in 3 mL PBS and in the presence of HPK (a radical photoactive initiator) for approximately 10 seconds.

The gels were incubated at 37° C. At various time points the PBS was removed and frozen while 3 mL fresh PBS was added. Rhodamine was encapsulated in a similar fashion.

C. Measuring Swell Volume

The equilibrium swelling volume, Q, correlates to the crosslinking density of a hydrogel. The higher the crosslinking density of a hydrogel, the less volume of water (or other solvent) the network is able to absorb. Gels were swollen in 3 mL phosphate buffered saline (PBS). Swollen weights increased and stabilized after 2 days. The equilibrium swelling volume, Q was calculated using the 2 day swelling weight.

Figure 3:
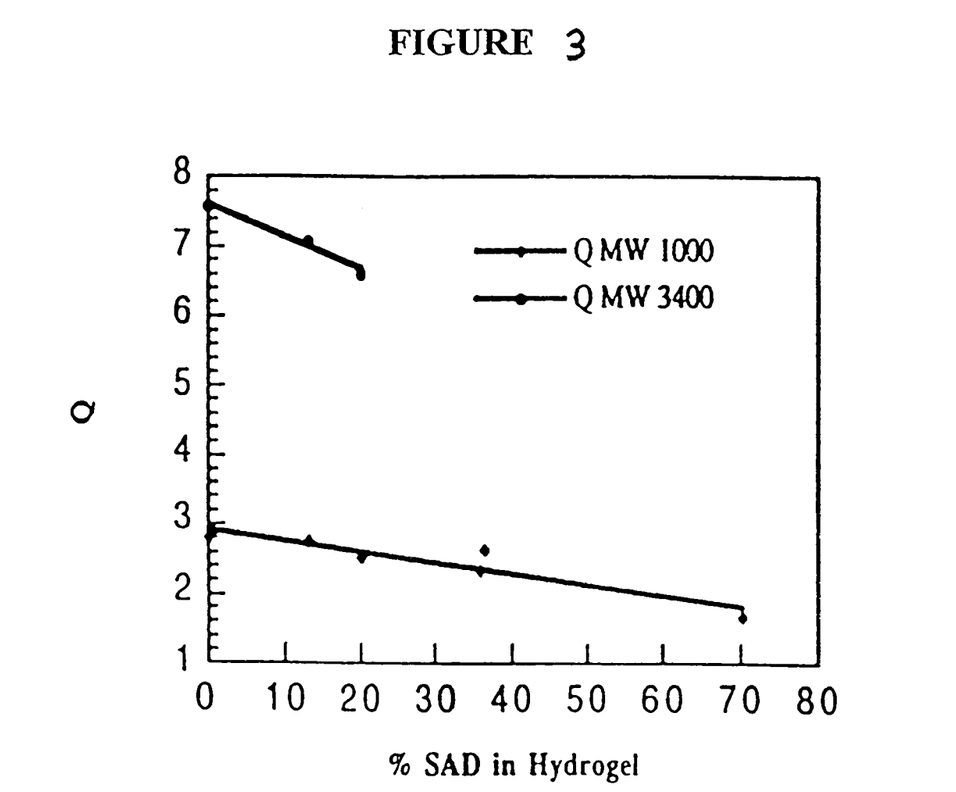
FIG. 3 graphically depicts the effect of succinic acid (SAD) concentration on the equilibrium swelling volume of a polymer, for polymers of molecular weight 1000 and 3400.

Q was calculated for hydrogels ranging from 0 to 70% SAD using PEOD of MW 3400 and MW 1000. As predicted, as SAD concentration increases, Q decreases. Hydrogels synthesized from the lower MW PEOD (1000) had lower Q values (FIG. 3).

D. Measuring Release of Compound

Figure 4:
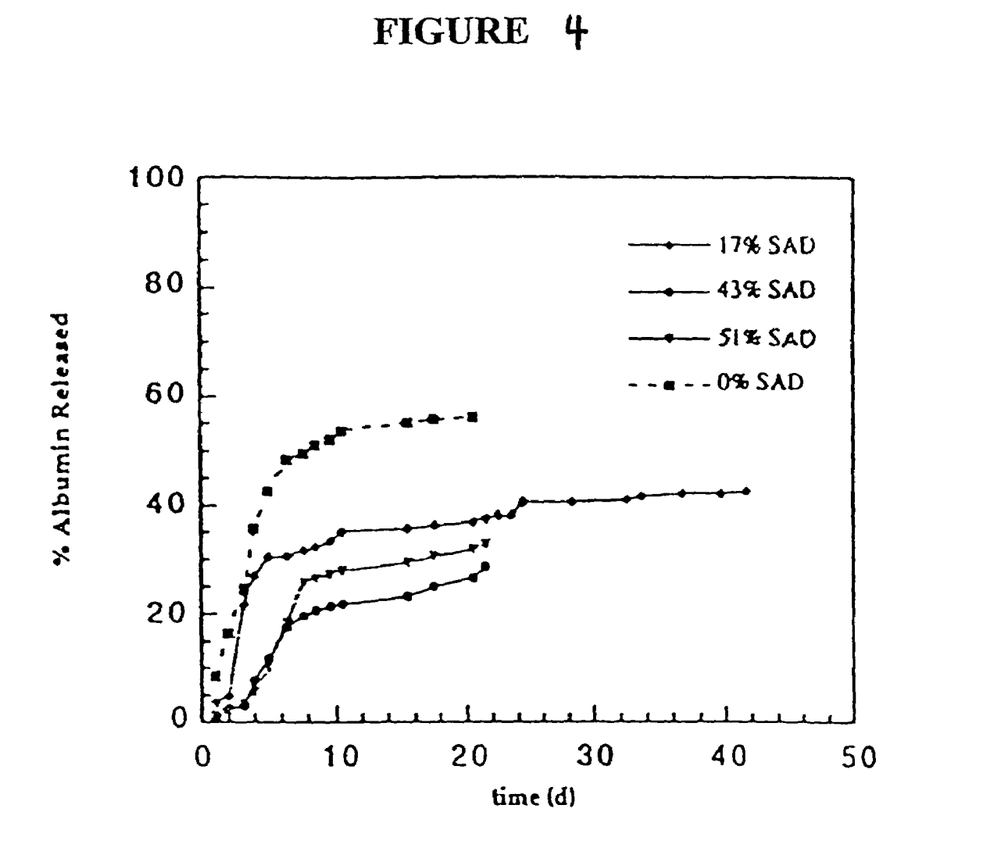
FIG. 4 graphically depicts the effect of succinic acid concentration (17%, 43%, 51%, and 0% SAD) on release of serum albumin (percent) from a polymer over time (days).

The effect of varying SAD hydrogel concentrations on controlled release of albumin was studied. Levels of BSA was quantified using a micro-BSA assay (Pierce) and release was observed by fluorimetry. FIG. 4 shows release profiles for hydrogels with 0, 15, 17, 43 and 51% SAD for up to 40 days. All gels exhibited an initial fast release for the first 10 days. The percent of albumin released at the 10 day time point varied with SAD. The 43 and 51% SAD gels released only 25% of the encapsulated albumin while the 0% SAD gel released 50%. After 10 days the 0% SAD gel released very low levels of albumin while the gels with SAD released on average 1% albumin per day for up to 40 days.

Figure 5:
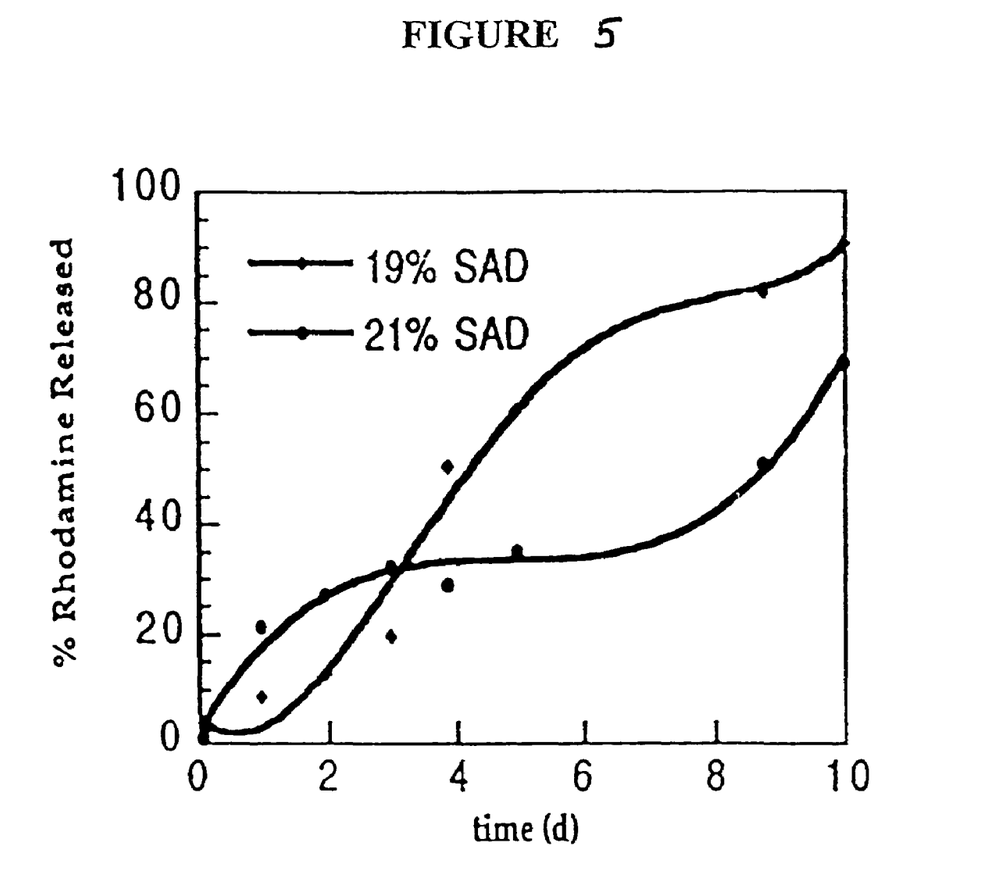
FIG. 5 graphically depicts the effect of succinic acid concentration (19% and 21% SAD) on the release of rhodamine from a polymer (percent over time in days).

Rhodamine (MW 479) was used to study the release of a small molecule for the initial fast release 10 day phase. Hydrogels with 20% SAD released 70-90% of the encapsulated rhodamine during this time period (FIG. 5).

Thus, cogelation of dimethacrylate succinic acid and poly (ethylene oxide) yields a hydrogel which can slowly release molecules such as rhodamine and albumin. Varying the concentration of succinic acid in the hydrogels is a means to further control the hydrogel swelling and release characteristics.

Example 4

Ex Vivo and In Vivo Tissue Engineering

In this example, the use of photopolymerizable solutions for tissue engineering was studied ex vivo and in vivo. For both the ex vivo and in vivo studies, articular cartilage from the knee, hip and shoulder joints of a pig were dissected for underlying bone, cut into small chips and isolated by incubation with collagenase. Chondrocytes were isolated by differential centrifugation. The isolated chondrocytes were washed and cell number was determined using a hemacytometer.

A. Ex Vivo

While the polymers PEO and PEOD can be used in vivo and shows good biocompatibility, the biocompatibility of the initiator was examined in vitro using bovine chondroycytes. Although the initiator PHK is approved for dental applications, the initiator was examined without the presence of polymer to ascertain the toxicity of the radical produced to initiate a photopolymerization. The PEOD is very reactive towards the radical so the lack of polymer would make all radicals available to damage cells (a worst case scenario). Three initiator concentrations (0.1, 0.05 and 0.01% (w/w)) were examined.

Chondrocyte isolated from calf shoulders were maintained ex vivo in cell culture medium (DMEM) at 37° C. and 5% $CO_2$. Cells were passaged approximately once a week. Approximately 10,000 cells per well in an 8-well tissue culture plate were seeded. 1-hydroxycylcohexyl-phenyl-ketone (HPK) was added to DMEM to reach 0.1, 0.05 and 0.01% (w/w) concentrations. The cells were incubated for 24 hours in the present of the initiator to examine possible acute cell toxicity. The cells were then exposed to UVA radiation (2 $mW/cm^2$) for 3 minutes to activate the photoactive initiator.

To determine the effect of photoactive initiator concentration on cells before exposure to light, cells were exposed to a concentration of 0% (w/w), 0.1% (w/w), 0.05% (w/w), and 0.01% (w/w). Little difference is observed between all cases showing that the initiator does not appear to be toxic before exposure to light.

The effect of photoactive initiator concentration on cells after exposure to light for four days was determined by exposing cells to a concentration of 0% (w/w), 0.1% (w/w), 0.05% (w/w), and 0.01% (w/w). The cells were compared morphologically and in relation to cell proliferation for 4 days. After light exposure comparable to that which is needed in vivo to cause polymerization (3 minutes at 1-3 $mW/cm^2$), extensive cell death is observed at an initiator concentration of 0.1%. Variable damage is observed at 0.05% and no damage was observed morphologically between the control and the 0.01% cells. Four days after light exposure the 0.01% and control cells had shown similar proliferation.

Further analysis was made between controls which were a) not exposed to initiator or UVA, b) cells exposed to UVA only and c) cells exposed to UVA in the presence of 0.01% PHK. The effect of photoactive initiator on cells when exposed to no light or photoactive initiator, light only, 0.01% light and initiator, and 24 hours after light exposure was determined. This dose of initiator does not appear to alter proliferation and morphology.

B. In Vivo

The time of degradation of polymer scaffold for tissue engineering is important. While it is not necessary to understand the precise mechanism, it is believed that the proliferating cells need room to multiply and form tissue yet young tissue needs protection from mechanical forces in order to maintain shape. Chondrocytes form neocartilage in only one week when injected alone or with PEG. Therefore it is desirable to have a fast degrading or eroding tissue engineering scaffold.

While space is needed for the growing tissue, structural support is necessary to maintain construct shape in the presence of the various mechanical forces of surrounding tissue including the skin. The desire for a scaffold with a fast degrading component and one to maintain structural integrity which is injectable led to the use of semi-interpenetrating networks (semi-IPN).

In this example, the polymer used consisted of 35% PEOD which covalently reacts together to form a porous network in the presence of light. The remaining 65% consisted of PEO MW 100,000 which does not chemically react to form a network, but is trapped within the network formed by PEOD forming a semi-IPN.

This system provides a twofold degradation. The PEO can diffuse form the network but the covalently connected PEOD must have ester bonds broken before the PEOD chains can be released and excreted. This chemical degradation is slow but may be accelerated by the production of enzymes such as esterases by neocartilage.

For the in vivo studies, the chondrocyte were centrifuged and brought up to a volume to make a concentration of $50 \times 10^6$ cells in 900 microliters. A 35% ratio of methacrylated to nonmethacrylated polymer (Shearwater Sciences, Huntsville, Ala.) was used. 70 milligrams of PEOD (molecular weight 3400, Shearwater Polymers, Huntsville, Ala.) and 130 milligrams of PEO (molecular weight 100,000 Sigma Chemical, Steizenhofen, Germany) were dissolved in 900 microliters of cells ($50 \times 10^6$) and media and 100 microliters of 1 mg/ml PHK to form a 20% polymer solution.

Three athymic female mice (Massachusetts General Hospital, Boston, Mass.) were anesthetized with methoxyflurane and 0.1 milliliter or polymer/chondrocyte solution was injected in four regions subcutaneously using a 22 gauge needle. It was then necessary to show that the cells survived injection and transdermal polymerization. A nude mouse was injected twice with injections similar to those in the cell/polymer implants described below. The mouse was then placed under a lamp emitting UVA radiation. Mice received a light intensity of 1-3 $mW/cm^2$ as measured by a radiometer for 3 minutes. The polymer/chondrocyte construct could be palpated to observe polymerization progression.

A mouse was sacrificed at each of one, two and three weeks and the four constructs were removed and fixed in 10% phosphate buffered formalin for 24 hours. Specimens were embedded in paraffined sections. The sections were subsequently stained with hematoxylin and eosin (H&E) and Safrinin O according to standard histological technique.

Four constructs per mouse were harvested at 1, 2 and 3 weeks. H&E staining and Safranin O staining of the implants after one week shows that at one week, islands of proliferating chondrocytes are observed. Safranin O stain shows the production of GAG, a product of differentiated chondrocytes. At two weeks, the cells are surrounded by basophilic tissue similar to that of neocartilage. Safranin O staining shows further production in GAG compared to 1 week.

Modifications and variations will be obvious to those skilled in the art from the foregoing detailed description. Such modifications and variations are intended to come within the scope of the appended claims.

We claim:

1. A method for making semi-interpenetrating or interpenetrating polymer networks, comprising: exposing a suspension of dissociated cells in a solution of two or more biocompatible polymers to free radicals generated during photopolymerization using a light source external to the suspension so that the light generates free radicals thereby forming the semi-interpenetrating or interpenetrating polymer networks.

2. The method of claim 1, wherein the semi-interpenetrating or interpenetrating polymer networks are cartilage tissue equivalents.

3. The method of claim 2 wherein the light is selected from the group consisting of ultraviolet radiation, long-wavelength ultraviolet radiation, and visible light.

4. The method of claim 2 wherein the suspension further comprises a photoinitiator.

5. The method of claim 4 wherein the photoinitiator is selected from the group consisting of erythrosin, phloxime, rose bengal, thonine, camphorquinone, ethyl eosin, eosin, methylene blue, riboflavin, 2,2-dimethyl-2-phenylacetophenone, 2-methoxy-2 phenylacetophenone, 2,2-dimethoxy-2-phenylacetophenone, and other acetophenone derivatives.

6. The method of claim 5 wherein the suspension further comprises a cocatalyst.

7. The method of claim 6 wherein the cocatalyst is selected from the group consisting of N-methyl diethanolamine, N,N-dimethyl benzylamine, triethanolamine, triethylamine, dibenzylamine, N-benzylethanolamine, and N-isopropyl benzylamine.

8. The method of claim 7 wherein the cocatalyst is triethanolamine.

9. A method of forming a tissue equivalent in a subject, the tissue equivalent comprising semi-interpenetrating or interpenetrating networks, comprising:
   injecting a suspension of dissociated cells in a solution of two or more biocompatible polymers into a subject, and
   exposing the suspension to free radicals generated during photopolymerization using a light source external to the injected suspension so that the light penetrates through tissue to generate free radicals thereby forming the tissue equivalent.

10. The method of claim 9 wherein the x-rays, ultrasound, infrared radiation, far infrared radiation, ultra-violet radiation, long-wavelength ultraviolet radiation, or visible light is applied externally to the skin.

11. The method of claim 9 wherein the light is selected from the group consisting of ultra-violet radiation, long-wavelength ultraviolet radiation, or visible light and is applied within a synovial space to a polymer-cell suspension injected into an adjacent joint.

12. A method of forming a tissue equivalent in a mold, the tissue equivalent comprising semi-interpenetrating or interpenetrating polymer networks, comprising:
   injecting a suspension of dissociated cells in a solution of two or more biocompatible polymers into a mold, and
   exposing the suspension to free radicals generated during photopolymerization using a light source external to the suspension so that the electromagnetic radiation generates free radicals thereby fong the tissue equivalent.

* * * * *